United States Patent
Tirapu Azpiroz

(10) Patent No.: US 9,739,751 B2
(45) Date of Patent: Aug. 22, 2017

(54) DEVICES FOR TRAPPING AND CONTROLLING MICROPARTICLES WITH RADIATION

(71) Applicant: INTERNATIONAL BUSINESS MACHINES CORPORATION, Armonk, NY (US)

(72) Inventor: Jaione Tirapu Azpiroz, Rio de Janeiro (BR)

(73) Assignee: International Business Machines Corporation, Armonk, NY (US)

(*) Notice: Subject to any disclaimer, the term of this patent is extended or adjusted under 35 U.S.C. 154(b) by 255 days.

(21) Appl. No.: 14/615,169

(22) Filed: Feb. 5, 2015

(65) Prior Publication Data

US 2016/0231274 A1 Aug. 11, 2016

(51) Int. Cl.
| | |
|---|---|
| *G01N 29/00* | (2006.01) |
| *G01N 27/447* | (2006.01) |
| *B01L 3/00* | (2006.01) |
| *B03C 5/00* | (2006.01) |
| *B03C 5/02* | (2006.01) |

(52) U.S. Cl.
CPC .. *G01N 27/44791* (2013.01); *B01L 3/502715* (2013.01); *B01L 3/502761* (2013.01); *B03C 5/005* (2013.01); *B03C 5/02* (2013.01); *G01N 27/44713* (2013.01); *B01L 2200/0647* (2013.01); *B01L 2300/0645* (2013.01); *B01L 2300/0816* (2013.01); *B01L 2300/0864* (2013.01); *B01L 2300/0877* (2013.01)

(58) Field of Classification Search
CPC G01N 27/447–27/44795; B01D 57/00–57/02; C02F 1/4696; B81B 1/00–1/008
USPC ............... 204/450–470, 546–550, 600–621, 204/643–645
See application file for complete search history.

(56) References Cited

U.S. PATENT DOCUMENTS

| | | | |
|---|---|---|---|
| 5,304,486 | A | 4/1994 | Chang |
| 7,931,792 | B2 | 4/2011 | Fiechtner et al. |
| 8,021,532 | B2 | 9/2011 | Hunt et al. |
| 8,262,885 | B2 | 9/2012 | Hunt et al. |
| 8,630,807 | B2 | 1/2014 | Edman et al. |
| 2002/0192112 | A1* | 12/2002 | Chow ............... B01L 3/502715 422/63 |

(Continued)

FOREIGN PATENT DOCUMENTS

JP 2008245593 10/2008

OTHER PUBLICATIONS

Khoshmanesh, K. et al. "Size based separation of microparticles using a dielectrophoretic activated system" Journal of Applied Physics 108, 034904 (2010); doi: 10.1063/1.3457226. Aug. 2010. (9 Pages).

(Continued)

*Primary Examiner* — Bach Dinh
(74) *Attorney, Agent, or Firm* — Tutunjian & Bitetto, P.C.; Louis J. Percello

(57) ABSTRACT

A particle manipulation device includes a substrate and a microchannel included in the substrate and configured to receive a fluid including particles therein. A biasing structure is formed on the substrate adjacent to, but outside the microchannel. The biasing structure is configured to dispense radiation at a frequency to bias movement of the particles within the microchannel from outside the microchannel.

25 Claims, 8 Drawing Sheets

(56) References Cited

U.S. PATENT DOCUMENTS

| | | |
|---|---|---|
| 2009/0211910 A1 | 8/2009 | Hunt et al. |
| 2009/0219647 A1 | 9/2009 | Hunt et al. |
| 2011/0162966 A1 | 7/2011 | Burke et al. |
| 2014/0209463 A1 | 7/2014 | Gibson et al. |
| 2014/0216935 A1 | 8/2014 | Vezenov |
| 2015/0198517 A1* | 7/2015 | Simpson ............ G01N 15/1459 209/552 |

OTHER PUBLICATIONS

Feiginov, M., et al. "Resonant-tunnelling-diode oscillators operating at frequencies above 1.1THz" Applied Physics Letters 99, 233506 (2011); doi: 10.1063/1.3667191. Dec. 2011. (4 Pages).

Chiou, P., et al. "Massively parallel manipulation of single cells and microparticles using optical images" Nature Publishing Group. vol. 436. No. 21. Jul. 2005. (4 Pages).

Chiou, P. "A Novel Optoelectronic Tweezer Using Light Induced Dielectrophoresis" 2003 IEEE/LEOS International Conference on Optical MEMS. Aug. 2003. pp. 8-9.

Chou, C., et al. "Electrodeless Dielectrophoresis of Single- and Double-Stranded DNA" Biophysical Journal, vol. 83 Oct. 2002. pp. 2170-2179.

Chou, C., et al. "Electrodeless Dielectrophoresis for Micro Total Analysis Systems" IEEE Engineering in Medicine and Biology Magazine. Nov./Dec. 2003. pp. 62-67.

Cummings, E., et al. "Dielectrophoresis in Microchips Containing Arrays of Insulating Posts: Theoretical and Experimental Results" Analytical Chemistry, vol. 75, No. 18, Sep. 2003. pp. 4724-4731.

Ding, X., et al. "On-chip manipulation of single microparticles, cells, and organisms using surface acoustic waves" PNAS, vol. 109. No. 28. Jul. 10, 2012. pp. 11105-11109.

Edwards, B., et al. "Electric tweezers: negative dielectrophoretic multiple particle positioning" New Journal of Physics 14 (2012) 063012 (13pp). Jan. 2012. pp. 1-13.

Gascoyne, P., et al. "Microsample preparation by dielectrophoresis: isolation of malaria" Lab Chip, 2002, May 2, 2002. pp. 70-75.

Grier, D. "A Revolution in Optical Manipulation" Dept. of Physics, James Franck Institute and Institute for Biophysical Dynamics, The University of Chicago. May 2013. pp. 1-10.

IBM News Room. "Made in IBM Labs: IBM Scientists Unveil Highly Integrated Millimeter-Wave Transceiver for Mobile Communications and Radar Imaging applications" </http://www-03.ibm.com/press/us/en/pressrelease/41225.wss/> Jun. 2013. (2 Pages).

Hu, S., et al. "A SiGe BiCMOS Transmitter/Receiver Chipset With On-Chip SIW Antennas for Terahertz Applications" IEEE Journal of Solid-State Circuits, vol. 47, No. 11. Nov. 2012. pp. 2654-2664.

Ishigaki, K., et al. "Direct intensity modulation and wireless data transmission characteristics of terahertz-oscillating resonant tunnelling diodes" Electronics Letters, vol. 48 No. 10. May 2012. (2 Pages).

Maestrini, M., et al. "A 2.5-2.7 THz Room Temperature Electronic Source" 22nd International Symposium on Space Terahertz Technology. Apr. 2011. pp. 1-4.

Momeni, O., et al. "High Power Terahertz and Millimeter-Wave Oscillator Design: A Systematic Approach" IEEE Journal of Solid-State Circuits, vol. 46, No. 3. Mar. 2011. pp. 583-597.

Sugiyama, H., et al. "Room-temperature Resonant-tunneling-diode Terahertz Oscillator Based on Precisely Controlled Semiconductor Epitaxial Growth Technology" NTT Technical Review, vol. 9 No. 10 Oct. 2011. pp. 1-7.

Tek, F., et al. "Computer vision for microscopy diagnosis of malaria" Malaria Journal, vol. 8, No. 153. Jul. 2009. pp. 1-14.

Temiz, Y., et al. "Dielectrophoretic Trapping of Beads in Compact Capillary-Driven Systems With Multi Wall Electrodes" 17th International Conference on Miniaturized Systems for Chemistry and Life Sciences. Oct. 2013. pp. 979-981.

Yu, A., et al. "A Dual-Band Millimeter-Wave CMOS Oscillator With Left-Handed Resonator" IEEE Transactions on Microwave Theory and Techniques, vol. 58, No. 5. May 2010. pp. 1401-1409.

Zheng, L., et al. "Towards Single Molecule Manipulation with Dielectrophoresis Using Nanoelectrodes" 2003 Third IEEE Conference on Nanotechnology. Aug. 2003. pp. 437-440.

Wanke, M., et al. "Transceivers to Conquer the Terahertz Frontier" </http://spectrum.ieee.org/semiconductors/devices/transceivers-to-conquer-the-terahertz-frontier/> Aug. 2011. (7 Pages).

Hellemans, A. "Reecord-Setting Terahertz Transmitters" </http://spectrum.ieee.org/semiconductors/devices/recordsetting-terahertz-transmitters/> Jan. 2012. (4 Pages).

Armstrong, C. "The Truth About Terahertz" </http://spectrum.ieee.org/aerospace/military/the-truth-about-terahertz/> Aug. 2012. (4 Pages).

Anthony, S. et al. "Terahertz wireless chip brings 30Gbps networks, subcutaneous scanning" </http://www.extremetech.com/extreme/106771-terahertz-wireless-chip-brings-30gbps-networks-subcutaneous-scanning/> Nov. 2011. (3 Pages).

* cited by examiner

DEVICES FOR TRAPPING AND CONTROLLING MICROPARTICLES WITH RADIATION

BACKGROUND

Technical Field

The present invention relates to particle manipulation devices, and more particularly to devices having paths and mechanisms for trapping and controlling microparticles and microorganisms as well as radiation generating electronic circuits for biasing of the microparticles.

Description of the Related Art

Point of Care (PoC) devices have increased in the interest for microfluidics-based devices. Microfluidics-based devices have the potential to perform entire biological experiments or immunological tests on a single credit card-sized or even smaller chip. PoC devices provide miniaturized laboratories for fast, inexpensive, easy to use, portable tests, such as e.g., blood sugar testing and the like.

Techniques exploiting dielectrophoretic (DEP) forces have emerged as a powerful touch-less method for cell and particle discrimination, separation, isolation or concentration, useful for sample processing. The dielectrophoretic (DEP) forces arise from interactions of field-induced charge polarization in cells or particles with field inhomogeneity that acts to attract (or repel) cells to (or from) electric field maxima for positive (or negative) dielectrophoresis forces. An electrically polarizable object will be trapped in a region of a focused electric field. These forces depend not only on the geometrical configuration and excitation scheme of the electrode array but also on the dielectric properties of the cell or particle and of its suspending medium. The magnitude, direction and frequency dependencies of DEP responses depend on the composition, size and conductivity of both particle and medium.

DEP has been employed for the separation of live from dead yeast cells, live from dead bacteria cells, malaria-infected cells from healthy cells, and human leukemia cells from healthy blood cells. For example, the membrane of red blood cells (erythrocytes) turn very permeable to ions when they become infected by malarial parasites, resulting in the loss of internal ions to the low-conductivity suspending medium and a much lower internal conductivity as compared to healthy red blood cells.

One way to make a DEP trap is to create an electric field gradient with an arrangement of planar metallic electrodes in a channel. A form of electrode-less dielectrophoresis manipulation can be done through the use of a strongly focused beam of light, commonly known as "optical tweezers" or through a hybrid variation using photoconductive materials, the "optoelectronic tweezers". Intensity gradients in the converging beam draw small objects, such as a colloidal particle toward the focus, such that particles can be trapped in three dimensions near the focal point. They can operate by dynamically positioning potential energy minima and maxima.

While electrodeless DEP does not need metal evaporation during the fabrication, the structure is chemically inert with no impact on cell integrity or viability, and it avoids electrolysis at metal DEP electrodes with very high electric fields; this approach requires large, expensive, energy-intensive equipment that is external to the microchip and can only be used in a laboratory setting. Other electrode-less DEP structures involve changes in the microfluidic channel geometry such as constrictions or pillars.

SUMMARY

A particle manipulation device includes a substrate and a microchannel included in the substrate and configured to receive a fluid including particles therein. A biasing structure is formed on the substrate adjacent to, but outside the microchannel. The biasing structure is configured to dispense radiation at a frequency to bias movement of the particles within the microchannel from outside the microchannel.

Another particle manipulation device includes a chip including a substrate, a microchannel included in the substrate and configured to receive a fluid including particles therein; and at least one biasing structure formed on the substrate adjacent to but outside the microchannel. The at least one biasing structure is configured to dispense radiation at a frequency to bias movement of the particles within the microchannel from outside the microchannel. A control module includes a generation circuit configured to generate a signal for exciting the biasing structures.

A method for particle manipulation includes introducing a fluid having particles therein to a microchannel included in a substrate and configured to receive the fluid having the particles therein and biasing the particles traveling in the microchannel using at least one biasing structure formed on the substrate adjacent to but outside the microchannel, the at least one biasing structure being configured to dispense radiation at a frequency to bias movement of the particles within the microchannel from outside the microchannel.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1A:
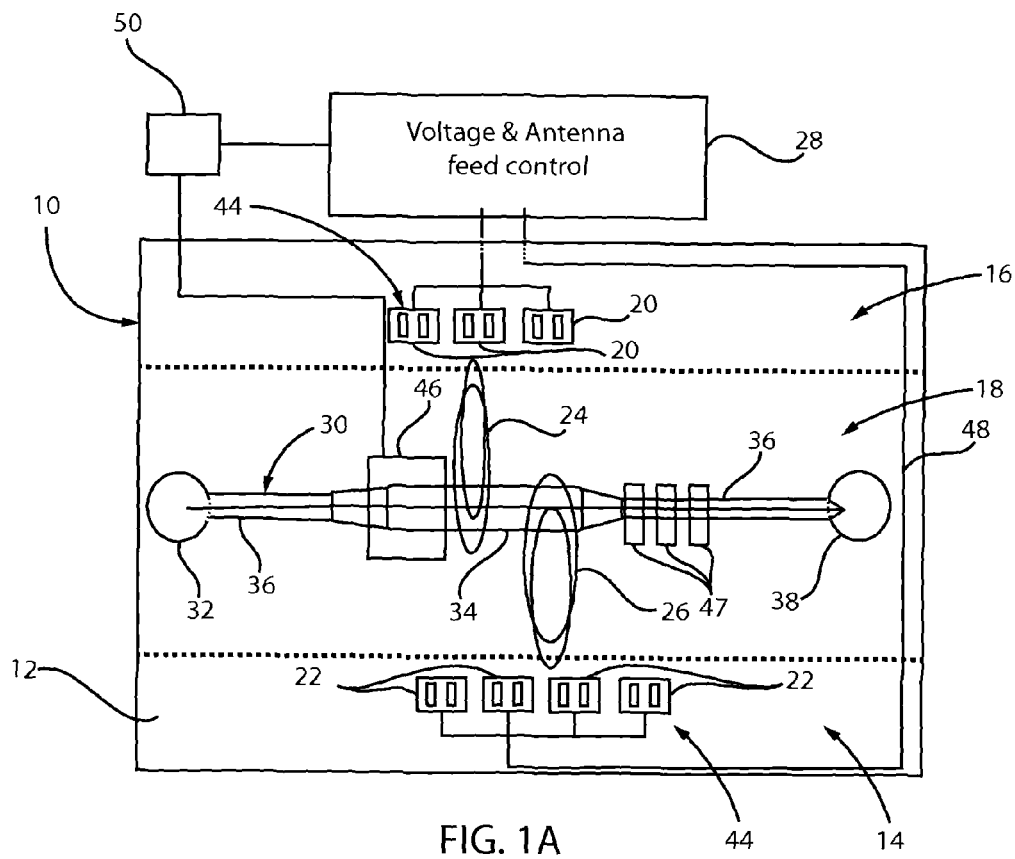
FIG. 1A is a top view of a particle manipulation device including a microchannel and electronic biasing structures on a same substrate or chip in accordance with the present principles.

In accordance with the present principles, devices and methods are described that eliminate the need for large, expensive and energy-intensive equipment for generating a focused beam of light in "optical tweezers" settings. In particularly useful embodiments, by incorporating electromagnetic radiating elements on a surface of a microfluidic chip, external to microchannel cavities, the challenges associated with in-situ electrodes in direct contact with the fluid are avoided. Microstrip patch antennas can be employed as inexpensive electromagnetic radiating elements and can be implemented on a surface of the chip with a ground plane on a bottom surface of a substrate of the chip, and a coaxial feeding line on a side of the chip or through the substrate.

In other embodiments, an antenna configuration and radiation pattern can be designed and optimized to perform any of the trapping, separation or concentration of microparticles or cells through dielectrophoresis (DEP). Antenna arrays with phased feeds can be employed to further optimize and enhance directivity of the radiation beam, or to permit real-time beam steering through control circuitry and semi-independent feeding of antennas. This provides flexibility to change the DEP functionality in real-time and provides a less expensive alternative to optical tweezers, even for disposable devices in Point of Care (PoC) applications.

Additional elements for focusing or guiding of electromagnetic waves may include electromagnetic band-gap structures, metamaterial components or surface plasmons inducing elements, which can also be incorporated into the chip. The electromagnetic radiation element (antenna) can also be implemented externally to the microfluidic chip, as part of a reader/controlling circuitry that is not necessarily in direct contact with the chip substrate. In-situ electrodes inside micro-channel can still also be employed for more advanced functionality.

The present principles may incorporate an in-situ image sensor array component (CMOS or CCD based), which can be either integrated into the device or integrated as part of an external reader and/or controlling circuitry, to capture real time images of the flow through the micro-channels. This image sensor can be connected with an image processing element that determines the status of the fluid flow in the channel and determines the proper feedback signal to be applied on the antenna feeding line that produces the optimum radiation pattern through a feedback control loop for real-time particle manipulation. The image sensor and image processing element can be used for detection or more accurate and precise diagnostic purposes. For example, malaria parasitized cell sorting and concentration through electromagnetic-based DEP and image capture and identification with image pattern recognition software.

Light waves are a form of high frequency electromagnetic wave carrying electric and magnetic energy through space. Lower frequency electromagnetic radiation can be generated through antennas which are electrical devices that convert electric power into electromagnetic waves in the radio, microwave and millimeter wave range (wavelengths down to 0.1 mm for THz radiation). Many structures, designs, materials and antenna sizes may be employed in accordance with the present principles. Antenna arrays enable higher directivity and steering capability of the radiation pattern. After particles or cells are processed (separated, concentrated, isolated, etc.) through DEP biasing methods, detection/recognition or diagnosis can employ other physical mechanisms or methods, for example, optical (fluorescence or colorimetric), magnetic, impedance or conductivity measurement, amperometric, mechanical, etc.

It is to be understood that the present invention will be described in terms of a given illustrative architecture for micro-fluidic devices on a substrate or a wafer; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

A design for an integrated circuit chip may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1B:
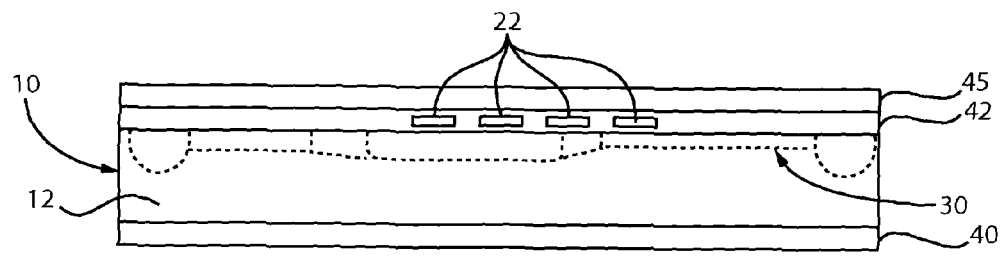
FIG. 1B is a side view of the particle manipulation device of FIG. 1A including a ground plane and other layers on the substrate or chip in accordance with the present principles.

Referring now to the drawings in which like numerals represent the same or similar elements and initially to FIGS. 1A and 1B, a top view (FIG. 1A) and a side view (FIG. 1B) are shown of an illustrative particle manipulation device 10 in accordance with the present principles. Device 10 may include a substrate 12 upon which a microfluidic chamber or channel 30 is formed in a first region or section 18, and second regions or sections 14 and 16 are configured for including biasing structures 44 for producing or radiating energy to bias particles in the channel 30. It should be understood that the second regions 14 and 16 may be formed on any portion of the substrate 12 including to the left of an inlet 32 to the right of an outlet 38 below the channel 30 (deeper into or on the other side of the substrate 12, etc.).

The microfluidic channel 30 is configured to receive particles, preferably in solution, and pass through the microchannel 30. During the passage of the particles through the channel 30, the particles are biased by the biasing structures 44, which may include, for example, antennae 20, 22. Biasing structures 44 are preferably circuits, transducer elements or other energy or radiation producing elements configured to change the movement of the particles or select a type of particles in the microchannel 30. Biasing includes speeding up, slowing down, changing direction, changing the energy (adding or removing energy), or any other change imparted to the particles to separate, distinguish or otherwise alter the motion of the particles.

The biasing structures 44 are depicted as antennae 20 and 22 controlled by a voltage and antenna feed control circuit 28. The circuit 28 may be integrated on the substrate 12 or may be provided externally to the device 10. In the example shown in FIG. 1A, the microchannel 30 includes antennae 20 on one side and antennae 22 on the opposite side. The antennae 20 and 22 are offset along a trap to affect the particles traveling through the microchannel 30 in different ways. Different types of radiation may be employed or different operating frequencies, voltages or other characteristic may be employed for operating structures 20 and 22. While two types of structures (20 and 22) are depicted any number of structures and modes or operation may be employed on a same device 10.

In one embodiment, particle or organism trapping (electromagnetic tweezers) could be achieved by the combination of the microfluidic chamber 30 and a series of THz antennas 20, 22 or antenna arrays designed and powered such that their radiation patterns 24, 26 are directed towards an observation chamber 34, and they produce constructive interference at a determined position on the chamber 34 where an organism will then be trapped through positive dielectrophoresis (e.g., where the organisms or particles are attracted to electric field maxima). An array of antennas (20, 22) can increase power and directivity, making the trapping beam narrower and sharper and create a more precise trapping spot. Real-time feedback can be achieved using the control circuit 28, which may include an image sensor such as a cell-phone camera that would capture images and generate the appropriate signal to adjust the amplitude and phase applied to feed each antenna element and move the trapping spot.

The substrate 12 may include silicon or other semiconductor material, e.g., II-VI, III-V, Ge, etc. The substrate 12 may include glass, ceramic, metal, polymer, organic polymer (e.g., PolyDimethylsiloxane (PDMS), a Si based organic polymer) or any other suitable material. In one embodiment, the control circuit 28 is integrated in the substrate 12 (e.g., silicon or glass) and the structures 44 include antennae/oscillators 20, 22 within a few $mm^2$ chip, which can be powered by a small battery (not shown) or through a connection to a portable device like a cell-phone or tablet which would be used to capture, process the image and produce the necessary signals to control the antenna feed 28. The microfluidic region 18 of the device 10 could be fabricated on a Si/Glass/PDMS substrate 12 and can be made detachable from the regions 14 and/or 16 holding the antennas 20, 22 such that only the microfluidic region 18 is made disposable.

In another embodiment, the microfluidic channel 30 may be formed using etching processes common to semiconductor processing and the circuits or structures 44 are integrated with the same substrate 12.

Laser components, optical lenses and filters are not needed to create the trapping force (although they may be employed and may be used for visualization in some embodiments).

The biasing structures 44 may take on many forms (e.g., antennae 20, 22, as described). Optimization algorithms in combination with rigorous electromagnetic solvers can be used to produce antenna designs with the corresponding amplitudes and phases to feed each antenna element to generate a desired radiation pattern, with the direction and angular extent, as desired. This optimization can be performed during an antenna design step. A set of feeding configuration options can be pre-determined during this design step that generates as many radiation patterns as needed or desired. The various feeding configuration options would then be saved in memory of the feed control 28 and be selected during device operation to change between radiation patterns or trapping position or strength.

In addition, some of the antennas 20, 22 can be configured as THz (or other frequency) detectors to extract parameters of the organism or particle under evaluation in the microfluidic channel or chamber 30 based on their scattering characteristics. Further, by designing broad band antennas 20, 22 capable of emitting wide bandwidths of wavelength, spectroscopic analysis of the sample can be performed to identify its precise components. Different cells, particles or elements have distinct signatures in the THz spectra, making THz spectroscopy useful to identification and imaging. These signatures allow the identification of many chemicals through their transmission spectra using THz multispectral images. THz imagers/detectors need good alignment to radiation, which is not a problem on a chip (substrate 12) where antenna elements 20, 22 are stationary.

By way of example, radiated power density can be defined as: $P_d=E\times H$ (Watts/m$^2$) or using H=E/h=E/120$\pi$: $|P_d|=EH=E^2/120\pi$. Power on an isotropic sphere is: $E^2/120\pi=P_T/4\pi r^2$. With E-field amplitude propagation losses ~1/r and E-power propagation losses ~1/r$^2$, $$E = \sqrt{\frac{120\pi P_T}{4\pi r^2}} = \frac{\sqrt{30 P_T}}{r} \text{ (V/m)}.$$

For propagation of laser beams r~100's of cm, and for propagation of THz beams on a chip, r~1 mm. Thus, propagation distances of a THz signal on a silicon chip surface can be of the order of 1-2 mm while the propagation distance of a laser beam on an optical tweezer setup is of the order of hundreds of cm's, plus the losses induced by filters and lenses required to focus the beam. Optical tweezers require much more powerful optical sources (orders of magnitude more power) than the device 10 in accordance with the present principles. Further, dielectrophoretic (DEP) force is proportional to the E-field gradient. A very sharp beam can produce strong DEP forces, E-field absolute strength is not as important as its sharpness.

In the THz range, the wavelength is of the order of a few hundred microns; hence the far field region of radiation is reached within a few hundred microns to a few mm within the chip or device 10. Operating within the far field region of radiation is preferred to avoid fringe field effects and sidelobes occurring in the near field, at distances close to the radiation elements. Hence, when using THz radiation, the microchannel 30 should be located at a few mm from the antenna radiation to allow for a distance at least 5 times the wavelength, and preferably 10 times the wavelength or more. High power THz radiation can achieve maximum powers in the 100's of microW to a few mW. THz radiation over very short distances can be used for arrays of antennas to radiate higher power while experiencing small attenuation since the propagation distances are very short.

Optical tweezers, on the other hand, require the laser light to travel longer distances and through several focusing and filtering elements, which attenuates the radiation power and, therefore requires light sources with higher power.

Numerous antenna design techniques and design optimization techniques can be employed to optimize a radiation pattern shape, direction, angular spread, and produce the proper shapes of each antenna radiating element and antenna array configuration (including the necessary amplitude and phase properties of the oscillation feeding each radiation element such as a patch or a slot antenna), which could be placed at any location within the chip 10.

Operating on the THz frequency range is preferred because it can produce more directed, narrower and, therefore sharper radiation patterns. The oscillator/antenna dimensions may be in the micro-scale and can compactly integrate arrays of large number of antennas, which can produce even higher intensities and sharper patterns. For example, millimeter and sub-millimeter (THz) electromagnetic wave radiation occurs between frequencies 30 GHz and 3 THz with wavelengths from 1 cm down to 100 microns. Electromagnetic oscillation can be generated most compactly through solid state diode sources, which can also be combined with multipliers or multiplexers to produce higher frequencies (e.g., Gunn diodes, GaAs Schottky, IMPATT, etc.). Electromagnetic energy is radiated in the desired direction through antennas 20, 22, including microstrip patch and slot antennas, which are compatible with, e.g., silicon substrates. Conductors of the antennas 20, 22 may include copper with a surface finishing of 3 to 5 μm nickel and a few hundred nanometers of gold. Other materials may also be employed.

The antenna design will determine radiation pattern, gain and directivity. Smaller dimensions are of interest for portable applications of dielectrophoresis effects with non-optical electromagnetic radiation, achievable with higher frequencies in the THz range. Smaller antenna and oscillator dimensions can be integrated on a chip or device and occupy smaller areas. Smaller antenna size allows for antenna arrays that will enable sharper radiation patterns with higher directivity to control micro-particles and higher radiation power. Sharper and more focused radiation patterns are important to produce larger electric field intensity gradients and, therefore larger DEP forces.

A distance between the antenna 20, 22 and the microfluidic channel 30 can be multiple times the wavelength (a few hundred microns), which helps with directivity since the radiation pattern will be in the far field or Fraunhoffer region of electromagnetic radiation, thus reducing effects of sidelobes and other undesired fringe effects characteristic of the near field region of radiation. THz sources may include resonant tunneling diodes (RTDs), which are the highest frequency active semiconductor devices that can oscillate in the THz range at room temperature. RTD oscillators are extremely compact sources of coherent continuous wave (CW) THz radiation and just a simple voltage source is needed to drive them. The THz sources may be integrated with resonators formed by slot antennas which help increase efficiency and output power. In other embodiments, Schottky diode-based multipliers may be employed as local oscillators in the submillimeter-wave range due to their compactness, electronic tunability and stability. These devices can deliver power, e.g., up to 1 mW at 2.5-2.7 THz.

THz photons are nonionizing, meaning they are not energetic enough to knock electrons off atoms and molecules in human tissue, which could trigger harmful chemical reactions. THz spectrometers can be used for identifying chemical composition or medical diagnostics. Recent advances in THz imaging sensors for medical diagnosis enable the combination of manipulation and imaging of organisms or microparticles DEP force can be provided for a spherical particle that becomes polarized inside a non-uniform electric field E as: $F_{DEP}=2\pi \in_m CM^* R^3 \nabla |E|^2$.

Polarized ions inside a particle can be modeled as a dipole, generating an electric field superposed to the original field. The polarized bead experiences a force which is a function of 3 factors: particle radius (R), Clausius-Mossotti factor (CM*) given by the relation $CM^*=(\in^*_p - \in^*_m)/(\in^*_p + 2\in^*_m)$ between the complex permittivity of the particle, $\in^*_p = \in_0 \in_p - j\sigma_p/\omega$, and that of the suspending medium, $\in^*_m = \in_0 \in_m - j\sigma_m/\omega$, and the distribution of electric field intensity ($\nabla E^2$). If the electric field surrounding the particle E is a constant then the DEP force is zero. Only non-uniform electric fields produce non-zero DEP forces. Combinations of DEP force with other forces affecting the particle (e.g., diffusion, capillary forces, gravity forces, Brownian motion, etc.) can serve to manipulate (trap, separate, convey, etc.) the particle as determined by the electric fields. By exploiting the dielectric differences between different particles or cells, DEP techniques can discriminate and sort the particles, for example, biological cells can be sorted based on differences in membrane properties (permeability, capacitance and conductivity), internal conductivity, size, etc.

DEP force depends on frequency of oscillation of the electric field. In lossy media, the complex permittivity of both particle and suspending medium are a function of frequency. At low frequencies ($\omega$), conductivity (free charge) or the imaginary component of the complex permittivity dominates, and at high frequencies ($\omega$), the real part of the complex permittivity dominates. In some examples, for instance a non-conducting bead in non-conducting water, the Clausius-Mossotti term is nearly constant with a value of CM*~−0.5, thus dealing negative DEP across all frequencies. For a conducting bead in non-conducting water, however, the conductivity dominates at low frequencies giving positive DEP (positive CM*), but the permittivity dominates at high frequencies, changing to negative DEP (negative CM*). For a conducting bead in conducting saline solution, a more complex relation is experienced. DEP force and sign depends on frequency and material properties.

DEP forces may be generated in a plurality of ways. Some of these may include the following. An electromagnetic radiation element on a surface of the microfluidic substrate 12 (chip), which is external to the microchannel 30 to also avoid the challenges associated with the use of in-situ electrodes in direct contact with the fluid. Electrodes in contact with the fluid channel may also be employed along with other features. Microstrip patch antennas 20, 22 can be employed as inexpensive electromagnetic radiating elements and can be implemented on the surface of the substrate 12 with a ground plane 40 on the bottom surface of the substrate 12 and a coaxial feeding line 48 on the side of the chip or through the substrate 12. Antenna configurations and radiation patterns can be optimized to perform any of the trapping, separation or concentration of micro-particles or cells through DEP. Antenna arrays with phased feeds can be employed to further optimize and enhance the directivity of the radiation beam or to allow real-time beam steering through control circuitry and semi-independent feeding of antennas, providing flexibility to change the DEP functionality in real-time.

Other elements for focusing biasing structures 44 may include electromagnetic band-gap structures, metamaterial components, surface plasmon inducing elements, acoustic energy producing elements (e.g., piezoelectric transducers), optical antennas or nanoantennas, electrodeless DEP elements, etc. Alternatively, the electromagnetic radiation element or biasing element 44 can be implemented externally to the microfluidic chip as part of a detection/controlling circuitry that is not necessarily in direct contact with the chip substrate. In-situ electrodes 47 may be employed inside or adjacent to the microchannel 30 and be used for more advanced functionality.

An in-situ image sensor array component 46 (e.g., CMOS or CCD based) may be integrated into the device 10 or as part of an external reader and controlling circuitry to capture real time images of the flow through the microchannel(s) 30. The image sensor 46 can be connected with an image processing element 50 that determines the status of the fluid flow in the channel 30 and determines the proper feedback signal to be applied on the antenna feeding line 48 to produce the optimum radiation pattern through a feedback control loop for real-time particle manipulation. In one embodiment, the image sensor 46 and the image processing element 50 can be used for detection for more accurate and precise diagnostic purposes.

The image processing element 50 may be integrated on the substrate 12 or may be connected externally. The image processing element 50 may include software for image pattern recognition or other image processing. In one embodiment, the image processing element 50 may be employed to analyze cells, e.g., to separate parasitized malaria cells versus healthy cells, for sorting and concentration through electromagnetic-based DEP and image capture and identification with image pattern recognition software on image processing element 50. Image processing element 50 may be integrated on the substrate 12 or be an external module.

Referring to FIG. 1B, the device 10 shows a microchannel or chamber 30 etched or otherwise formed in the substrate 12. This embodiment depicts electrodes (antenna) 22 formed on an insulating layer 42 which may be at or near a surface of the microchannel 30. Other layers 45 may be formed above or below the insulating layer 42.

Figure 2:
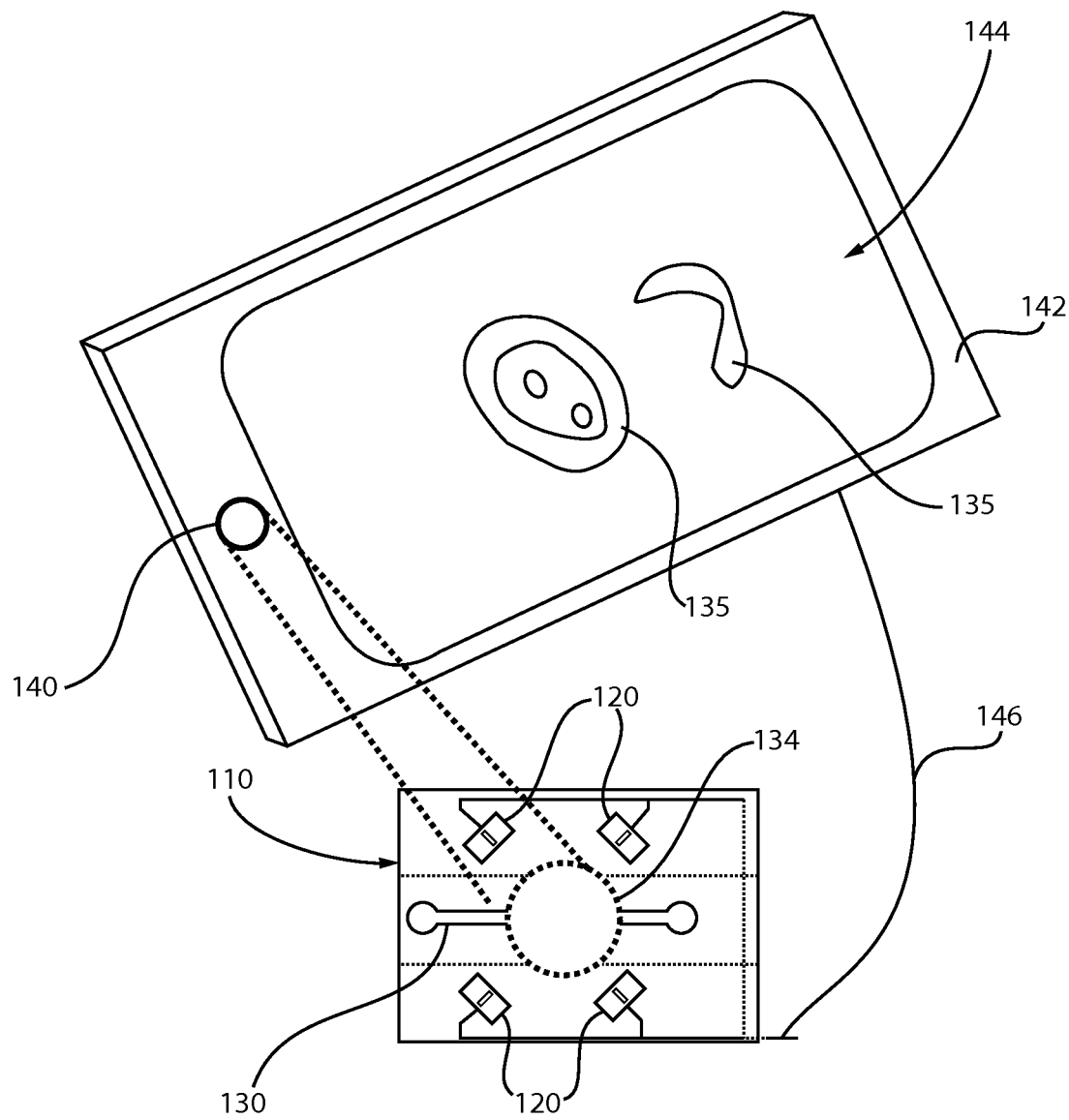
FIG. 2 is a perspective view of a particle manipulation device connected to a mobile device with an integrated image sensor, such as a smart phone, to view images, receive optical feedback and provide control signals for controlling biasing structures in accordance with the present principles.

Referring to FIG. 2, another device 110 includes a combination of a microfluidic chamber 130 and a series of THz antennas or antenna arrays 120 designed and powered in a way that their radiation patterns are directed towards an observation chamber 134 and they produce constructive interference at a determined position on the chamber 134 where an organism 135 will then be trapped through positive dielectrophoresis (where the organisms or particles are attracted to electric field maxima). The array of antennas 120 can increase power and directivity, making the trapping beam narrower and sharper and create a more precise trapping spot. Real time feedback can be achieved by the use of a simple image sensor such as a camera 140 on a cell-phone 142 or other external device. The camera captures images 144 and generates an appropriate signal on a feedback loop 146 to adjust the amplitude and phase applied to feed each antenna element 120 and move the trapping spot.

Figure 3:
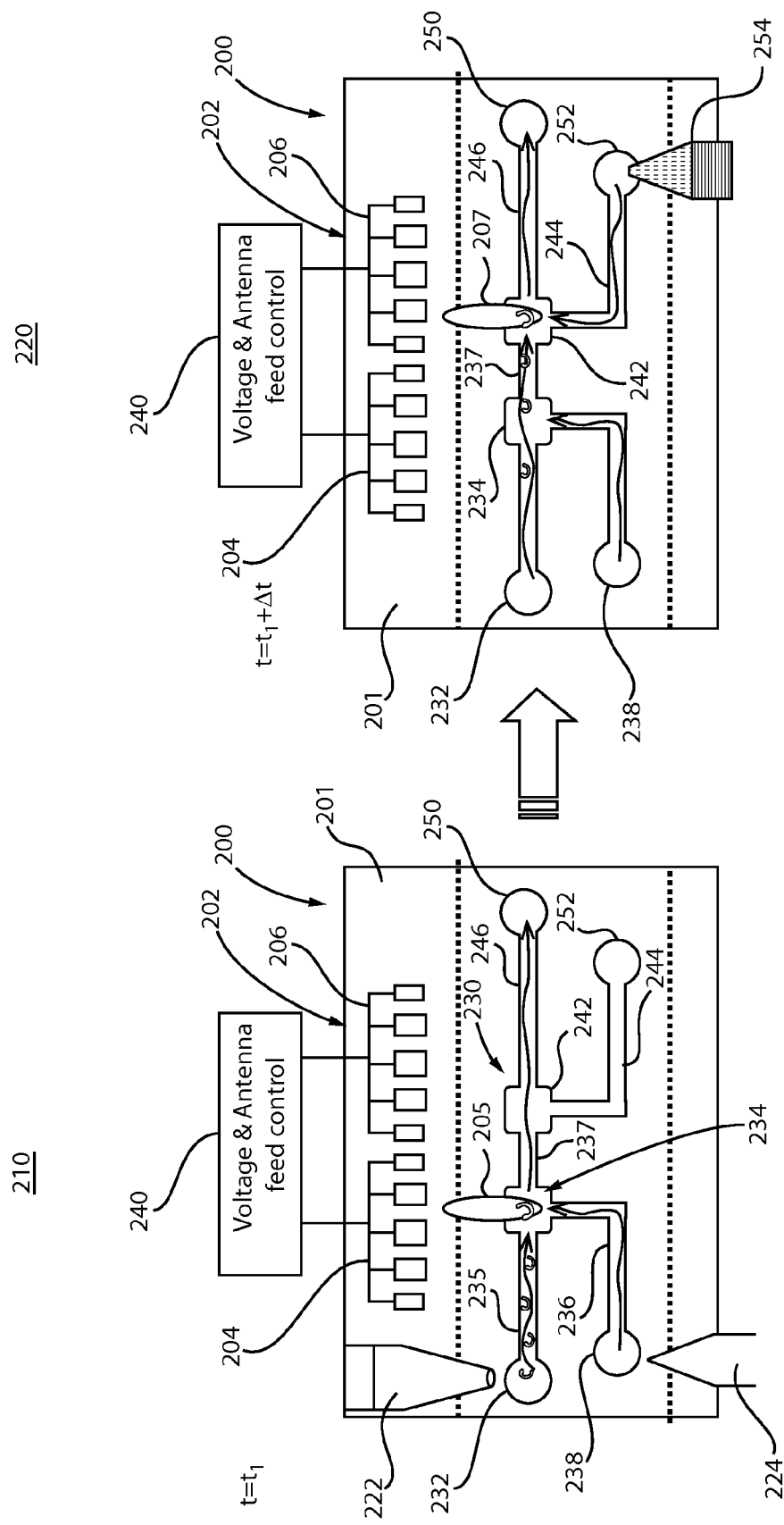
FIG. 3 shows top views of a particle manipulation device after two time periods showing a trapping operation followed by a rinsing operation in accordance with the present principles.

Referring to FIG. 3, in another embodiment, another device 200 includes a microfluidic channel 230 with a more complex structure having multiple chambers and paths formed on a substrate 201 (chip). The device 200 includes an electromagnetic radiation or biasing structure 202, which can be designed to perform several consecutive steps of a test or procedure on a single chip. The device is depicted at two instances during its operation.

In a first instance 210, a test may require that two or more fluids 222, 224 need to be mixed with a sample introduced at a sample inlet 232 (or one fluid used to rinse a target microorganism or particle from the other containing fluid). This organism travels down a channel 235 and is retained in a mixing chamber 234 through positive dielectrophoresis applied through an antenna array 204 that produces a radiation pattern 205 directed to the mixing chamber 234. The mixing chamber 234 is connected through another microchannel 236 to a second inlet 238 where a reacting substance (or rinsing substance) 224 is inserted, intended to be mixed with the target organism.

The antenna array 204 is connected to a small voltage generator 240 (with a small battery or via a mobile device attachment) and some circuitry to control the antenna feed (amplitudes and phases) such that the microorganisms or particles are trapped at the proper time ($t=t_1$).

In a second instance 220, the antenna array 204 is deactivated and an antenna array 202 is activated using generator 240 and some circuitry to control the antenna feed (amplitudes and phases). The first mixing chamber 234 is connected through another microchannel 237 to a second mixing chamber 242, which is also connected through microchannel 244 to a third inlet 252. Fluid 254 is introduced into a fluid inlet 252 to further rinse (or to insert a reacting substance to be mixed with) the specimens in the second mixing chamber 242. The antenna array 202 may be employed to trap and retain a different organism in chamber 242 for the duration of the rinsing (or reaction) step using radiation 207 induced DEP forces. The microchamber 242 is connected through a microchannel 246 with the outlet 250 for the retrieval of the reacted and rinsed microorganisms or elimination of unnecessary fluid. The microorganisms or particles trapped in microchamber 242 through radiation 207 are released to be allowed to move to the outlet 250 at the proper time ($t=t_1+\Delta t$) by turning off the radiation 207.

Figure 4:
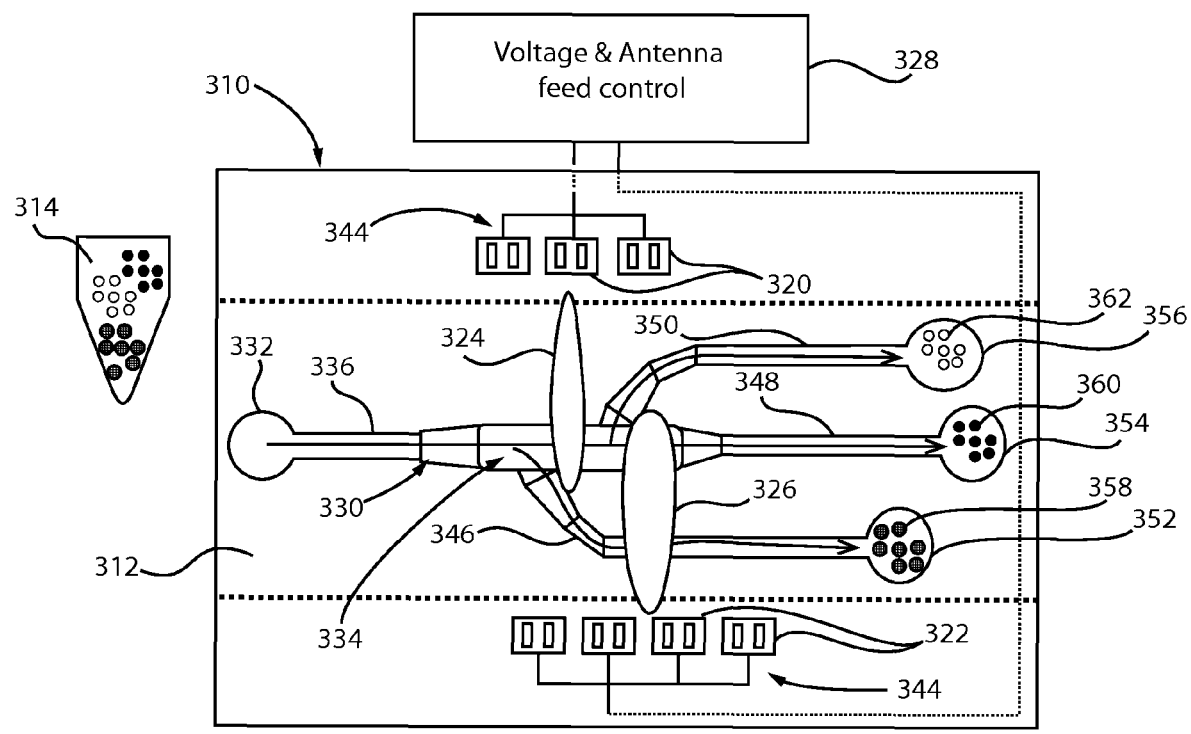
FIG. 4 is a top view of a particle manipulation device showing a multipath microchannel with electronic biasing structures for separating particles in accordance with the present principles.

Referring to FIG. 4, in another embodiment, another device 300 includes a microfluidic channel 330 with a more complex structure having multiple chambers and paths. The device 300 includes an electromagnetic radiation or biasing structure 344 that is designed along with the microfluidic channel 330 to separate particles of different size or composition through dielectrophoresis (e.g., negative DEP (neg-DEP) where the organisms or particles are repelled from electric field maxima). The neg-DEP force depends on the particle size ($R^3$) and composition (through its dielectric constant), hence particles of different sizes and/or composition can be separated by generating electric field patterns of varying strength. In this example, there are three channels 346, 348 and 350 configured to separate particles or cells 358, 360 and 362 into chambers or outlets 352, 354 and 356.

By creating side channels 346 and 350 from the main microchannel 348 towards which the different particles 358, 360 and 362 can be guided, a mix of particles 358, 360 and 362 can be separated by directing each type towards one of the side channels 346 and 350 or allowing the particles 360 to pass unaffected to chamber 354. Different radiation patterns 324 and 326 from various sets of biasing structures 344 such as antenna arrays 320 and 322 can be optimized to produce the necessary electric field strength at the corresponding channel bifurcations.

In one illustrative embodiment, a fluid 314 including particles 358, 360 and 362 is introduced at inlet 332 and flows through a path 336 to a separation chamber 334. Particles 358 are most sensitive to DEP force. This type of bead is repelled by the first electromagnetic beam 324 created by a first set of antennas 320 and moved towards the first side channel 346. Particles 362 are passed unaffected through the first DEP inducing beam 324 because the force strength was not stronger than the fluid drag. This could be due to the particle size not being large enough. This particle type (362) however is affected by the beam 326 produced by a second set of antennas 322 producing a stronger DEP force, and being directed towards the second side channel 350. Particles 360 pass unaffected through both DEP induced beams 324, 326, possibly due to a small size that makes the DEP force much weaker than the drag force of the fluid. The paths 350, 348 and 346 can branch off from a separation chamber 334 at different locations or may be disposed in other orientations as needed.

As before, the antennae 320 and 322 are controlled using a voltage and feed control circuit 328. Circuit 328 may be integrated into the chip or device 310 or may be connected externally. In one embodiment, different circuits 328 may be interchangeably connected to the chip 310 to provide different functions or controls to the biasing structures 344. In another embodiment, the circuit 328 may provide controls for adjusting the voltage, phase and other characteristics of the biasing structures 344 for controlling the timing, power, radiation (shape), etc. a priori or in real-time. The controls may be based on feedback, such as visual feedback (image sensors or other sensors, e.g., temperature, flow, etc.).

Figure 5:
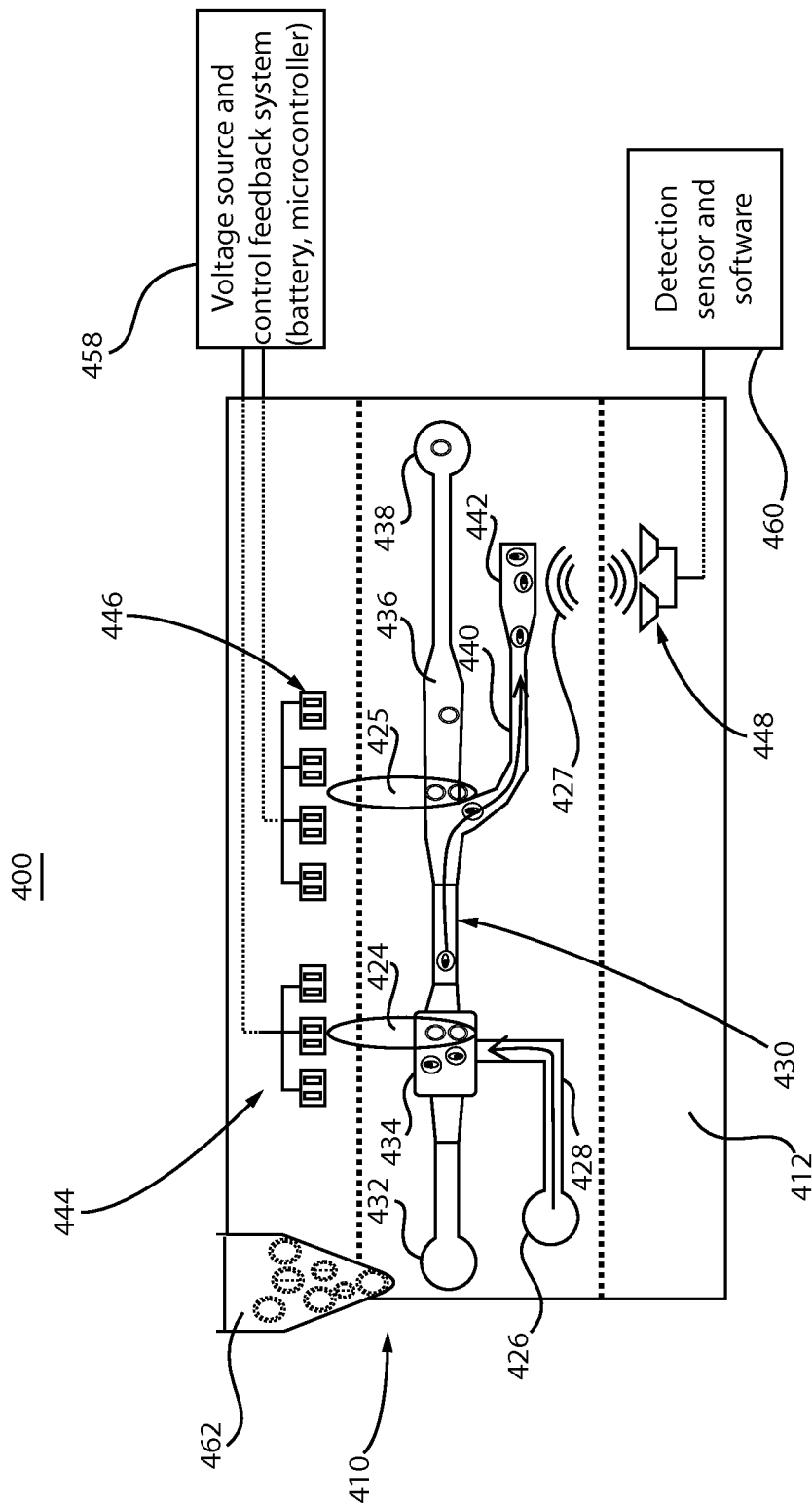
FIG. 5 is a top view of a particle manipulation device having a sensor and detection chamber in accordance with the present principles.

Referring to FIG. 5, another device 400 includes a chip 410 having a combination of a microfluidic chamber 430, a number of biasing structures 444 and 446 and a detection sensor 448. The device 400 will be illustratively described in terms of performing a test for red blood cells infected by malaria.

It is known that healthy red blood cells retain ions inside the cells and present a higher conductivity, leading to a positive-DEP response. The outer membrane of infected red blood cells, on the other hand, is compromised and unable to retain ions inside the cell, hence presenting low conductivity and a negative-DEP response. This means that healthy blood cells will be trapped by high intensity E-fields while infected blood cells will be repelled by high intensity E-fields. This difference in behavior can be used to separate healthy from infected red blood cells within microfluidic channels 436 and 440.

The testing device 400 includes a staining or rinsing chamber 434, where the fluid for staining or rinsing of the red blood cells can be mixed with the sample, to either help with later visualization (when optical detection or diagnosis is used, either manual or computerized) or to eliminate spurious elements in the sample that could compromise the measurement that can be performed inside the observation chamber 442. For example, the rinsing fluid can be inserted from a rinsing inlet 426 into the mixing or rinsing chamber 434 that also receives a sample fluid 462 containing the red blood cells (healthy and infected) from an inlet chamber 432.

Biasing structures 444 may include a set of antennas designed and located such that a radiation pattern 424 is directed towards the mixing or rinsing chamber 434 so that both healthy cells and infected cells are trapped inside the chamber 434. Healthy cells will be trapped within the radiation pattern maxima while unhealthy cells will be prevented from moving forward because they are repelled by the radiation pattern maxima.

This rinsing chamber 434 is connected to a second microchannel 428 that communicates with the inlet 426 where the rinsing or staining fluid is inserted into the chip 410 and flows toward the rinsing chamber 434 where red blood cells are being retained. Unhealthy cells cannot flow towards this secondary channel 428 because the fluid is flowing in the opposite direction, that is, towards the chamber 434.

The antenna arrays 444, 446 within the chip 410 are connected to a voltage generator circuit 458 or a battery controlled by a feedback system that turns the array on and off for a predetermined time.

A second step in the test performed in the microfluidic channel 430 separates the healthy from infected red blood cells taking advantage of the different DEP responses exhibited by each of these types of cells. Infected cells are rejected from a high intensity E-field and can be guided towards a separate channel 440 towards a final observation chamber 442. Similarly, the antenna array 446 produces a necessary electric field pattern 425 and is connected to the voltage generator 458 and controlled through feedback circuitry that determines timing.

The infected cells are guided towards the observation chamber 442 where detection will be carried out by a sensor 448 in one of several possible methods. For example, optical detection may be performed using an image sensor (448) focused on the observation chamber 442 with a transparent top cover. Another option may include using another set of THz antennas (448) to perform detection of scattered waves 427 from the contents inside the observation chamber 442 to determine its composition. THz spectroscopic analysis can provide precise identification of the sample composition and can thus produce not only a diagnosis but even identify the strain and degree of the infection. Other sensors 448 may also be employed. The radiation pattern 425 generated by the antenna array 446 can be designed to be of an intensity lower to that of radiation pattern 424 generated by the antenna array 444 so that the DEP force produced is not enough to overcome the hydrodynamic drag force and, therefore healthy cells flow through the separation chamber 436 unaffected to an outlet chamber 438.

For an accurate diagnosis, the detection sensor 448 produces a signal (from the optical or THz sensor) that is to be processed and contrasted against a database, through the use of a program stored in a signal processing unit 460 connected or integrated on the chip 410.

Variations of the device 400 can be envisioned to perform other tests or experiments. For example, an immunoassay test can be performed to detect diseases such as e-Coli or the common flu by the use of functionalized micro-particles or beads with antibodies that are mixed with the sample (blood or other fluids) within a vial and then inserted into the microchannel 430 through the inlet 432. The beads can then be trapped within a chamber (e.g., 434) with an antenna array 444 radiation pattern 424 directed towards the chamber exit that prevents the beads from continuing through microchannel 430. The secondary inlet 426 and microchannel 428 connected to the same trapping chamber 434 are employed to insert labeled (e.g., magnetic, colorimetric, fluorescent) antibodies and allowed to mix for some time with the trapped functionalized beads in chamber 434. The beads can then be allowed to proceed through channel 436 and guided with negative DEP towards the observation chamber 442 for detection. Another rinsing step can also be included. Detection can be performed by using THz detection with the corresponding signal processing software. Alternatively, optical or magnetic detection are also contemplated.

Figure 6:
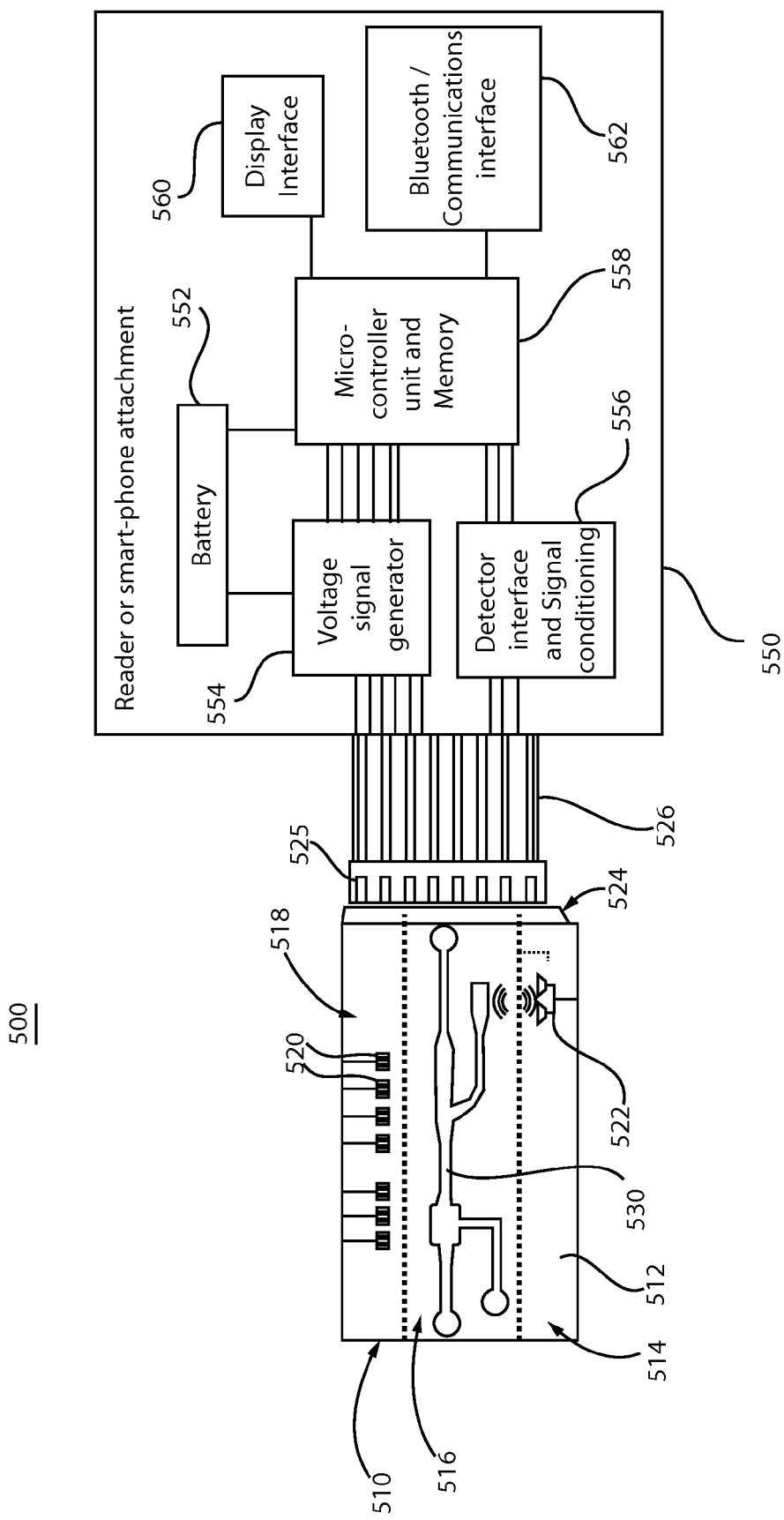
FIG. 6 is a top view of a particle manipulation device connected to an external control and data processing system or device, referred to as a reader, in accordance with the present principles.

Referring to FIG. 6, a device 500 is illustratively shown. The device 500 may be employed for field testing or may be incorporated into a point or care (PoC) device. Applications may include water testing, blood testing, quality testing in factory environments, etc. The device 500 includes a chip 510 having a microfluidic channel 530, biasing structures 520 and a detection sensor 522. For illustration purposes, chip 510 may be considered to be similar to device 400. The biasing structures 520 may include different types of structures and provided different types of radiation or energy. Similarly, the detection sensor 522 may be an image sensor, or may include another set of THz antennas to perform detection of the scattered waves, or can comprise other types of detection mechanisms (e.g., magnetic, impedimetric, etc.). The biasing structures 520 and detection sensor 522 are provided on a substrate 512. The channel 530 may be formed on the substrate 512 or may be formed on a separate substrate 516 so that it can be removed and disposed of. In other embodiments, the entire chip 510 may be disposable. The microfluidic channel 530 can be fabricated in a way that can be inserted into the substrate 512, which includes the biasing structures 520, detection sensor 522 inside a larger device housing (with biasing elements non-disposable). Alternatively, all components of the "microfluidic and radiation chip 510 can be integrated into a same substrate for a one-time use and be made disposable.

The device 510 includes an electrical contact portion 524 configured to connect with the biasing structures 520 and detection sensor 522 to control the biasing structures 520 and control and collect data from the detection sensor 522 and any other devices or components on the chip 510. An electrical connector 525 detachably connects to the electrical contact portion 524 of the chip 510 and may include a ribbon or other cable 526 to interface with a reader device 550.

The reader device 550 may include a specially designed device or may employ the functionality of an existing device, such as, e.g., a smart phone, computer or other computing device configured to interface with and control the chip 510. The reader device 550 may include a portable energy source 552 although other energy sources may be employed (e.g., outlet power, solar power, etc.). The reader device 550 includes a processor or microcontroller 558. The microcontroller 558 includes memory for storing programs, protocols and/or control features. In one embodiment, a voltage signal generator 554 is controlled by the microcontroller 558 to provide power signals to the biasing structures 520 on the chip 510. A detector or sensor interface 556 is included to control and receive feedback from the detection sensor 522, such as images or sensed parameters to provide for adjustments in the voltage signals from the voltage signal generator 554 as processed by the microcontroller 558.

The reader device 550 may include other features such as a display interface 560 for displaying images or connecting to a display for rendering images or other information. A communications interface 562 may be included for communicating with other devices or networks. For example, the interface 562 may provide Bluetooth® or other communications links for downloading or uploading information or programs as needed. The reader device 550 may be a modular, portable element, that is, a separate reader or a smart-phone attachment. The reader element may include additional electronic modules or software applications with various functions.

Figure 7:
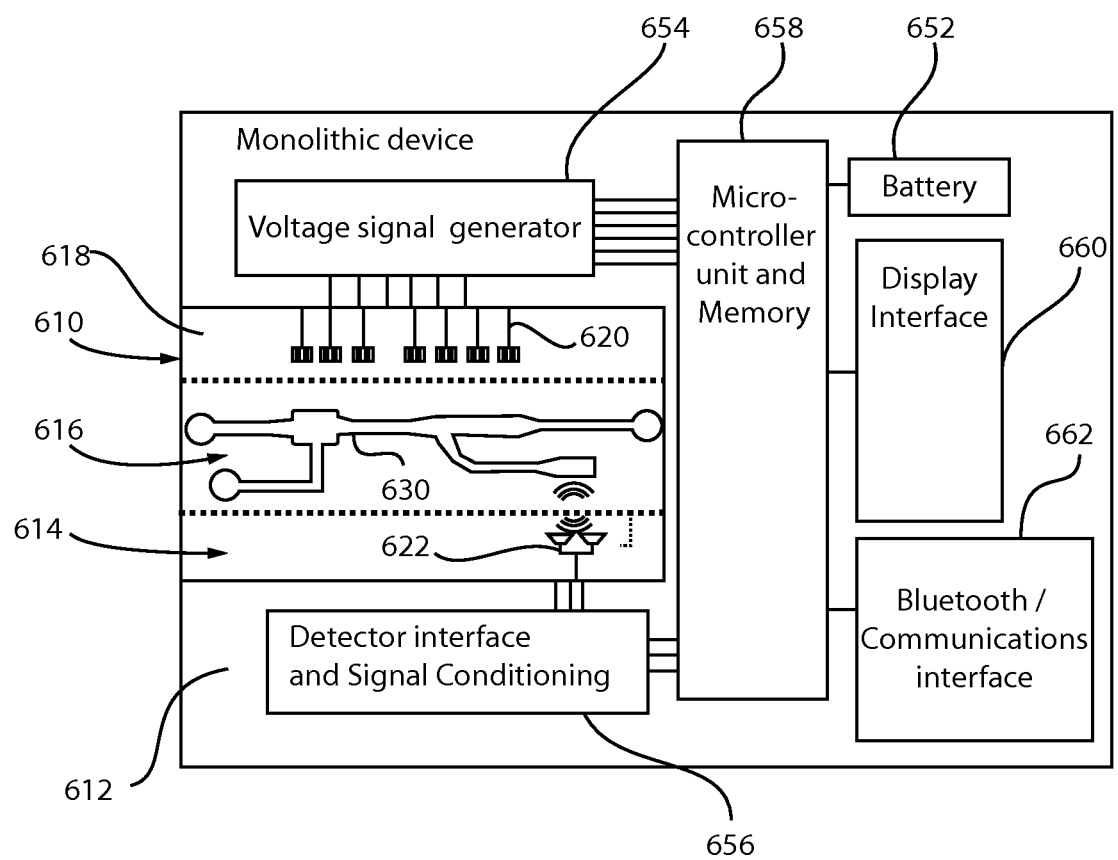
FIG. 7 is a top view of a particle manipulation device in combination with the reader elements fabricated as a monolithic structure on a chip or substrate in accordance with the present principles.

Referring to FIG. 7, a device 600 is illustratively shown. The device 600 may be employed for field testing or may be incorporated into a PoC device. Applications may include water testing, blood testing, quality testing in factory environments, etc. The device 600 includes a chip 610 having a microfluidic channel 630, biasing structures 620 and detection sensor 622. The biasing structures 620 may include different types of structures and provide different types of radiation or energy. Similarly, the detection sensor 622 may be an image sensor, or may include another set of THz antennas to perform detection of the scattered waves, or can comprise other types of detection mechanism (e.g., magnetic, impedimetric, etc.). The biasing structures 620 and detection sensor 622 are provided on a substrate 612. The channel 630 may be formed on the substrate 612 or may be formed on a separate substrate 616 so that it can be removed and disposed of.

The device 600 may be monolithic including all microfluidic, radiation and electronic elements in a single non-disposable chip. The electronic modules may include a voltage signal generator 654 (similar to generator 554, FIG. 6) to feed the biasing structures/elements 620 with varying amplitude and phase to create the appropriate radiation patterns. A detector interface and signal conditioning unit 656, similar to the interface 556 (FIG. 6) are provided. The appropriate detection sensing element 622 is included for optical, magnetic or other energy/radiation mechanism. If using THz imaging for detection, then a THz detector and its interface are provided. A microcontroller and memory 658 are included to execute programs, generate command signals and store the programs and results. A display unit or interface 660 may be included to show results to a user in real-time. A communications unit or interface 662 may be included with, e.g., a Bluetooth® or other wireless or wired communication interface such that the results can be transmitted to a cellphone, a computer, a remote database, etc. A battery 652 or other power source may be included to power the device 600.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 8:
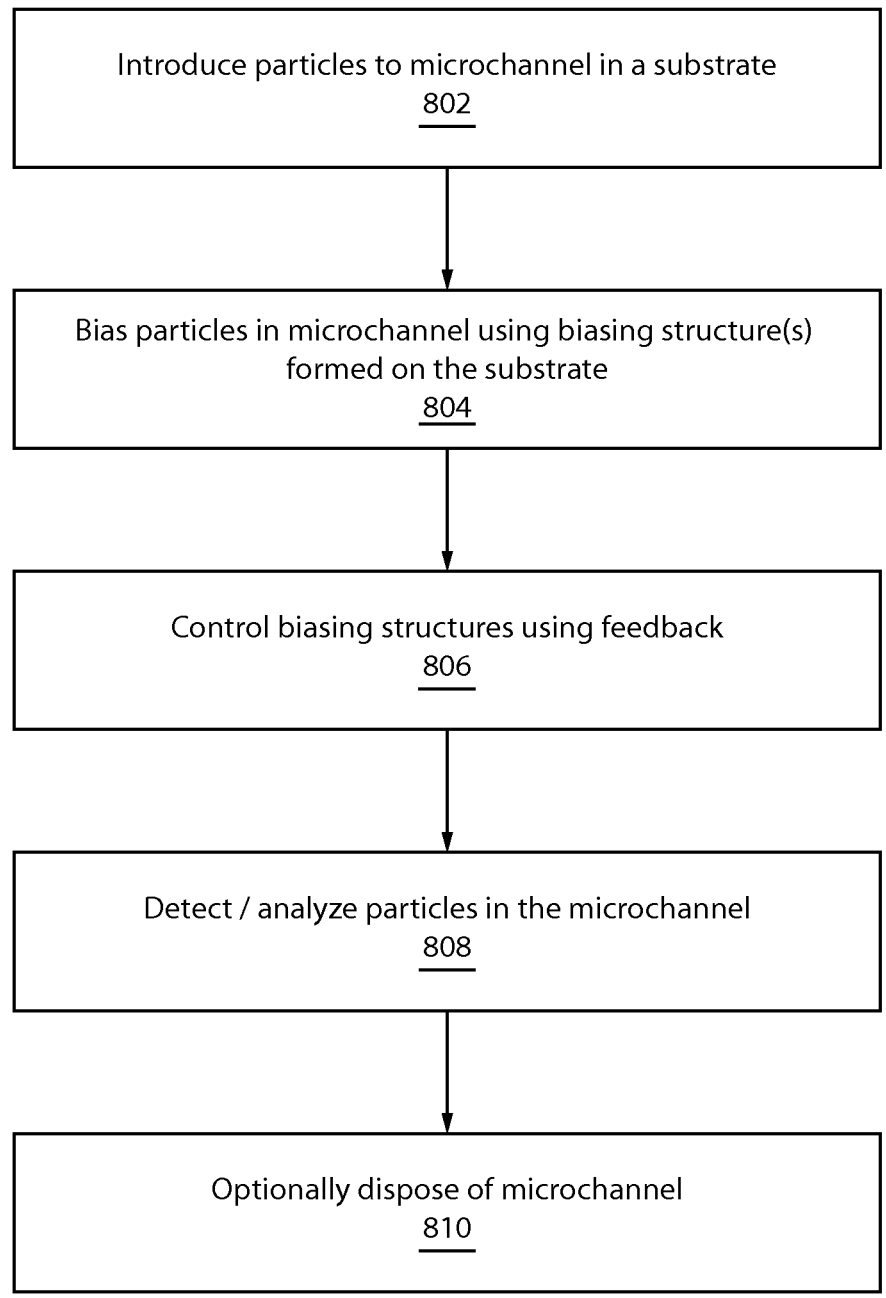
FIG. 8 is a block/flow diagram showing a particle manipulation process in accordance with illustrative embodiments.

Referring to FIG. 8, methods for particle manipulation are illustratively shown in accordance with the present principles. In block 802, a fluid having particles therein is introduced to a microchannel. The microchannel is included in a substrate and configured to receive the fluid having the particles therein. The microchannel may include one or more paths, traps, chambers configured to trap, separate or redirect particles biased by biasing structures.

In block 804, the particles traveling in the microchannel are biased using at least one biasing structure formed on the substrate adjacent to but outside the microchannel. The at least one biasing structure is configured to dispense radiation at a frequency to bias movement of the particles within the microchannel from outside the microchannel. In one embodiment, the biasing structure includes at least one antenna.

In block 806, radiation is generated to apply dielectrophoresis forces to the particles. The biasing structure or structures may be placed adjacent to the microchannel in a number of positions corresponding to chambers or pathways. The biasing structures are controlled by adjusting their power, phase or other characteristics. The biasing structures may be synchronized to perform different tasks while the particles move through the microchannel. For example, a first biasing structure may trap particles for observation, rinsing or other steps and a second biasing structure may separate particles of a certain type. The particles may be inorganic compositions, organic compositions, combinations of inorganic and organic materials, cells or other particulate matter.

The biasing structure(s) generate radiation to apply dielectrophoresis forces to the particles based on system feedback (visual feedback, sensor feedback, characteristics, etc.). The radiation may include one or more of terahertz range electromagnetic radiation, or include or be combined with acoustic energy transducers (e.g., piezoelectric materials) to generate acoustic waves, or include or be combined with magnetic field sources. Other types of energy and different frequency ranges may also be employed in accordance with the present principles.

In block 808, particles may be detected or analyzed using a sensor configured to detect characteristics of the particles. The characteristics may include motion of the particles, absorption spectra, fluorescence emission, magnetic properties, density, quantity, color, shape, and any other characteristic. The sensor may include an antenna, an image sensor, etc.

In block 810, the microchannel may be separable from the substrate, and may be disposed of after use. In one embodiment, the microchannel and the biasing structures are integrated on a same chip and the chip may be made disposable.

It should be understood that the present principles may be employed for field testing of cells, particulates in fluids, etc. In useful embodiments, the devices described here may be employed in Point of Care applications and may be used to determine or evaluate a number of diseases or conditions. In some embodiments, the microchannels where bodily fluid or contaminated fluids are placed can be disposable without disposing of the remaining structures of the device. It should also be understood that the components of the devices described herein may be combined in any combination to provide desired functionality.

Having described preferred embodiments for devices for trapping and controlling of microparticles with radiation (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims.

Having thus described aspects of the invention, with the details and particularity required by the patent laws, what is claimed and desired protected by Letters Patent is set forth in the appended claims.

What is claimed is:

1. A particle manipulation device, comprising:
   a substrate;
   a microchannel included in the substrate and configured to receive a fluid including particles therein; and
   at least one biasing structure comprising an antenna formed on the substrate adjacent to but outside the microchannel, the at least one biasing structure configured to generate radiation at a frequency to bias movement of the particles within the microchannel from outside the microchannel.

2. The device as recited in claim 1, wherein the microchannel includes a plurality of paths configured to separate particles biased by the biasing structures.

3. The device as recited in claim 1, wherein the microchannel includes at least one chamber for trapping particles biased by the biasing structures.

4. The device as recited in claim 1, wherein the microchannel includes at least one chamber for detecting particles, and the device further comprises an image sensor configured to detect characteristics of the particles in the at least one chamber.

5. The device as recited in claim 1, wherein the microchannel is integrated in a removable region that is separable from the substrate.

6. The device as recited in claim 1, wherein the at least one biasing structure includes at least one solid state diode source configured to use the generated radiation to apply dielectrophoresis forces to the particles.

7. The device as recited in claim 1, wherein the at least one biasing structure generates radiation to apply dielectrophoresis forces to the particles such that the particles are located in a far field region of the radiation.

8. A particle manipulation device, comprising:
   a chip including:
      a substrate;
      a microchannel included in the substrate and configured to receive a fluid including particles therein;
      at least one biasing structure comprising an antenna formed on the substrate adjacent to but outside the microchannel, the at least one biasing structure configured to generate radiation at a frequency to bias movement of the particles within the microchannel from outside the microchannel; and
   a control module including:
      a generation circuit configured to generate a signal for exciting the biasing structures.

9. The device as recited in claim 8, wherein the microchannel includes one or more of: a plurality of paths configured to separate particles biased by the biasing structures; at least one chamber for trapping particles biased by the biasing structures; or at least one chamber for detecting particles.

10. The device as recited in claim 8, wherein the control module and the chip are integrated on the substrate.

11. The device as recited in claim 8, wherein the control module and the chip are integrated together on a monolithic substrate.

12. The device as recited in claim 8, wherein the chip includes a detection structure integrated on the substrate and control module includes a detector interface for providing feedback to adjust the at least one biasing structure.

13. The device as recited in claim 12, wherein the detection structure includes at least one antenna configured to detect characteristics of particles in the microchannel.

14. The device as recited in claim 8, wherein the at least one biasing structure includes at least one solid state diode source configured to generate radiation to apply dielectrophoresis forces to the particles.

15. The device as recited in claim 8, wherein the at least one biasing structure generates radiation to apply dielectrophoresis forces to the particles such that the particles are located in a far field region of the radiation.

16. A method for particle manipulation, comprising:
   introducing a fluid having particles therein to a microchannel included in a substrate and configured to receive the fluid having the particles therein; and
   biasing the particles traveling in the microchannel using at least one biasing structure comprising an antenna formed on the substrate adjacent to but outside the microchannel, the at least one biasing structure being configured to generate radiation at a frequency to bias movement of the particles within the microchannel from outside the microchannel.

17. The method as recited in claim 16, wherein the microchannel includes one or more paths and chamber configured to trap, separate or redirect particles biased by the biasing structures.

18. The method as recited in claim 16, further comprising detecting particles using a sensor configured to detect characteristics of the particles.

19. The method as recited in claim 16, wherein the microchannel is separable from the substrate, and the method further comprising disposing of the microchannel after use.

20. The method as recited in claim 16, wherein the at least one biasing structure includes at least one solid state diode source, the method further comprising generating radiation to apply dielectrophoresis forces to the particles.

21. The method as recited in claim 16, wherein the at least one biasing structure generates radiation to apply dielectrophoresis forces to the particles such that the particles are located in a far field region of the radiation.

22. The device as recited in claim 3, wherein the biasing structures are configured to trap the particle in a position within the at least one chamber.

23. The method as recited in claim 17, wherein the biasing structures are configured to trap the particle in a position within the one or more paths and chamber.

24. The device as recited in claim 1, wherein the antenna comprises a resonant tunneling diode.

25. The device as recited in claim 8, wherein the antenna comprises a resonant tunneling diode.

* * * * *